(12) United States Patent
Oda

(10) Patent No.: US 8,246,347 B2
(45) Date of Patent: Aug. 21, 2012

(54) LOW PROFILE SELF-LIGATING ORTHODONTIC BRACKETS AND METHODS OF USING SUCH ORTHODONTIC BRACKETS

(75) Inventor: Todd I. Oda, Torrance, CA (US)

(73) Assignee: Ormco Corporation, Orange, CA (US)

( * ) Notice: Subject to any disclaimer, the term of this patent is extended or adjusted under 35 U.S.C. 154(b) by 167 days.

(21) Appl. No.: 12/718,513

(22) Filed: Mar. 5, 2010

(65) Prior Publication Data

US 2010/0159411 A1 Jun. 24, 2010

Related U.S. Application Data

(62) Division of application No. 11/685,540, filed on Mar. 13, 2007, now Pat. No. 7,674,110.

(60) Provisional application No. 60/743,700, filed on Mar. 23, 2006.

(51) Int. Cl.
*A61C 3/00* (2006.01)
(52) U.S. Cl. .......................................................... 433/10
(58) Field of Classification Search ................. 433/8–24
See application file for complete search history.

(56) References Cited

U.S. PATENT DOCUMENTS

| | | | | |
|---|---|---|---|---|
| 1,976,115 A * | 10/1934 | Boyd et al. | ...................... | 433/11 |
| 4,103,423 A * | 8/1978 | Kessel | .............................. | 433/10 |
| 4,547,153 A * | 10/1985 | Taylor | .............................. | 433/11 |
| 4,698,017 A * | 10/1987 | Hanson | ........................... | 433/11 |
| 5,908,293 A * | 6/1999 | Voudouris | ....................... | 433/10 |
| 6,168,428 B1 * | 1/2001 | Voudouris | ....................... | 433/11 |
| 6,325,622 B1 * | 12/2001 | Kelly et al. | .................... | 433/11 |
| 7,094,052 B2 * | 8/2006 | Abels et al. | ....................... | 433/8 |
| 2005/0239012 A1 * | 10/2005 | Bathen et al. | ................... | 433/10 |

* cited by examiner

*Primary Examiner* — Todd Manahan
*Assistant Examiner* — Matthew Nelson
(74) *Attorney, Agent, or Firm* — Wood, Herron & Evans, LLP

(57) ABSTRACT

Low profile self-ligating orthodontic brackets and methods of using such orthodontic brackets. The bracket includes a bracket body, a latching member, and a hinge pin pivotally coupling a hinged end of the latching member with the bracket body. The hinge pin, which is made of a resilient material, is configured to flex so that a portion of the latching member can be engaged with a recess defined in the bracket body to couple the non-hinged end of the latching member with the bracket body.

10 Claims, 11 Drawing Sheets

LOW PROFILE SELF-LIGATING ORTHODONTIC BRACKETS AND METHODS OF USING SUCH ORTHODONTIC BRACKETS

CROSS-REFERENCE TO RELATED APPLICATIONS

This application is a divisional of application Ser. No. 11/685,540, filed Mar. 13, 2007, which claims the benefit of U.S. Provisional Application No. 60/743,700, filed Mar. 23, 2006, the disclosure of each of which is hereby incorporated by reference herein in its entirety.

FIELD OF THE INVENTION

The invention relates generally to orthodontic brackets and, more particularly, to self-ligating orthodontic brackets and methods of using self-ligating orthodontic brackets.

BACKGROUND OF THE INVENTION

Orthodontic brackets represent principal components of all corrective orthodontic treatments devoted to improving a patient's occlusion. In conventional orthodontic treatments used for cosmetic enhancement of teeth, brackets are affixed to the patient's teeth and an archwire is engaged into a slot of each bracket. The archwire applies corrective forces that coerce the teeth to move into correct positions. The archwire forms a track to guide movement of the brackets and the associated teeth to desired positions for correct occlusion.

Self-ligating orthodontic brackets have been developed that eliminate the need for ligatures by relying on a movable cover, such as a slide, for captivating the archwire within the bracket's archwire slot. Self-ligating orthodontic brackets provide greater patient comfort, shorter treatment time, reduced chair time in the dental operatory, and more precise control of tooth translation. Traditional ligatures (e.g., elastomeric ligatures or metal wires) are also difficult to apply to each individual bracket, which is simplified by self-ligating types of orthodontic brackets. Elastomeric ligatures, which may be susceptible to decay and deformation, may also contribute to poor oral hygiene. Self-ligation also reduces the risks of soft-tissue injury to the patient's mouth.

Conventional self-ligating orthodontic brackets are relatively large in comparison to orthodontic brackets that are ligated conventionally using a ligature. The size discrepancy arises because of the need to engineer the moving parts of the self-ligation mechanism into the construction of the orthodontic bracket. The size difference also results in a relatively high physical profile for self-ligating orthodontic brackets as these brackets project a greater distance from the tooth surface than conventionally-ligated orthodontic brackets. The result of these deficiencies is that self-ligating orthodontic brackets have a higher physical profile that may result in patient discomfort, higher visibility, and poor patient hygiene.

Accordingly, there is a need for a self-ligating orthodontic bracket characterized by a low physical profile that overcomes these and other deficiencies of conventional self-ligating orthodontic brackets.

SUMMARY OF THE INVENTION

In one embodiment of the invention, an orthodontic bracket comprises a bracket body including a lingual surface configured to be mounted to a tooth, a labial surface, and an archwire slot in the labial surface. The orthodontic bracket further comprises a latching member coupled by a hinge pin with the bracket body for movement about an axis of rotation defined by the hinge pin. The latching member movable about the axis of rotation between an opened position in which the archwire is insertable into the archwire slot and a closed position in which the latching member retains the archwire in the archwire slot. When the latching member is in the closed position, the latching member is further movable relative to the bracket body in a non-collinear direction relative to the axis of rotation. The hinge pin is formed from a material having a flexibility sufficient to impart a spring bias to the latching member that opposes movement of the latching member in the non-collinear direction.

In another embodiment of the invention, a method is provided for using an orthodontic bracket having a bracket body and a latching member pivotally coupled with the bracket body for movement relative to the bracket body about an axis of rotation. The latching member is movable about the axis of rotation between an opened position in which the archwire is insertable into the archwire slot and a closed position in which the latching member retains the archwire in the archwire slot. The method comprises applying a force to the latching member generally in a non-collinear direction relative to the axis of rotation to move the latching member in the non-collinear direction against a spring bias directed generally opposite to the non-collinear direction.

The self-ligating mechanism of the orthodontic bracket may permit a decrease in the overall bracket height (i.e., the labial-lingual height). As a result, the orthodontic bracket may exhibit improved mechanics, aesthetics, patient comfort, and patient hygiene. The orthodontic bracket lacks a conventional moving slide but, instead, includes a pivoting latch as a self-ligating mechanism used to confine an archwire in the archwire slot. Because the self-ligating components of the orthodontic bracket are at the labial end of the bracket, the bracket may exhibit a relatively low profile when mounted to a tooth surface. As a specific example, the orthodontic bracket does not include a spring as a discrete component in the construction of the self-ligating mechanism.

BRIEF DESCRIPTION OF DRAWINGS

The accompanying drawings, which are incorporated in and constitute a part of this specification, illustrate embodiments of the invention and, together with a general description of the invention given above, and the detailed description given below, serve to explain the principles of the invention.

DETAILED DESCRIPTION

Figure 1:
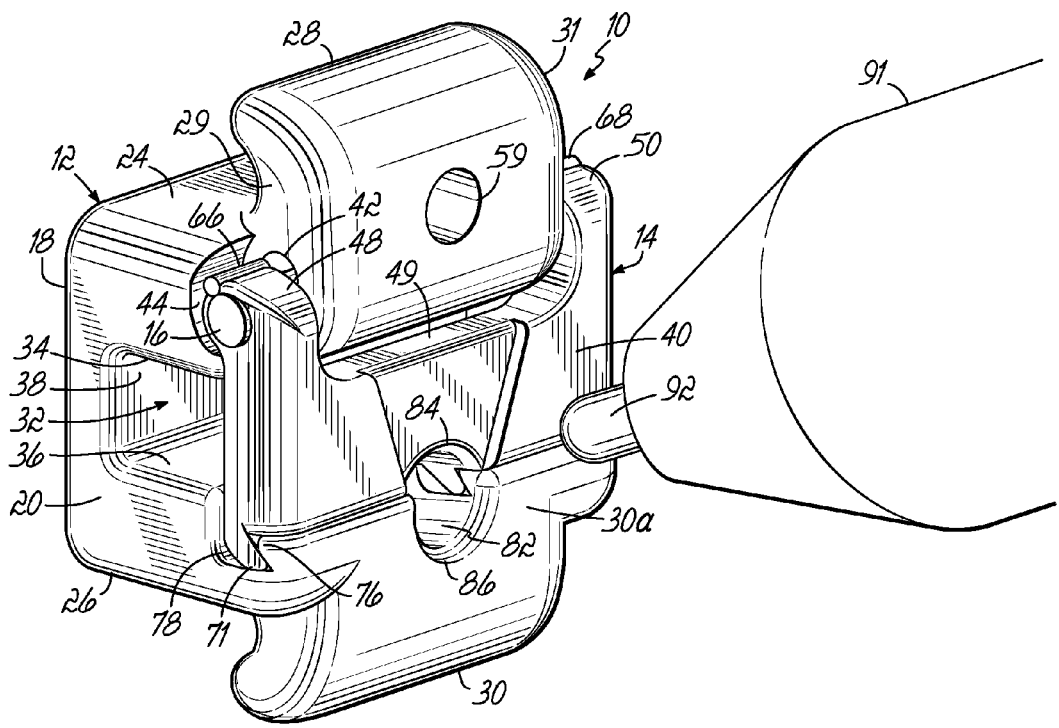
FIG. 1 is a perspective view of an orthodontic bracket in accordance with an embodiment of the invention in which a latching member of the orthodontic bracket is shown in a closed position.

With reference to FIGS. 1-5, an orthodontic bracket, generally indicated by reference numeral 10, for use in corrective orthodontic treatments generally includes a bracket body 12, a latching member 14, and a hinge pin 16 that couples the latching member 14 with the bracket body 12. The latching member 14 is hinged to the bracket body 12 by the hinge pin 16, which defines a shaft that allows the latching member 14 to swivel or pivot for moving the latching member 14 between an opened position (FIGS. 5, 6) and a closed position (FIG. 1). The angular range of pivoting movement of latching member 14 relative to the bracket body 12 may be less than 180° when the latching member 14 moves between the opened and closed positions. Portions of the hinge pin 16 also flex relative to the bracket body 12, as described below, to permit the latching member 14 to be locked with the bracket body 12 as the latching member 14 approaches the closed position and to be unlocked to release the latching member 14 from the closed position for pivoting movement to the opened position.

If orthodontic bracket 10 is mounted to a tooth in the maxilla, the latching member 14 may open in the occlusal direction. If orthodontic bracket 10 is mounted to a tooth in the mandible, the latching member 14 may open in the gingival direction. However, the invention is not so limited as the latching member 14 for different brackets 10 applied to either arch may open in any combination of directions.

The bracket body 12 and latching member 14 are constructed using known fabrication methods from conventional materials, including but not limited to a metal like titanium or a ceramic. The bracket body 12 and latching member 14 may be constructed of different materials or any combination of conventional materials familiar to a person having ordinary skill in the art. The hinge pin 16 may be fabricated from any suitable type of flexible material, such as a nickel titanium alloy.

The bracket body 12 has a bracket base 18 configured to be adhesive bonded to a buccolabial surface of a tooth (not shown) in any conventional manner such as, for example, with an appropriate orthodontic cement or glue. The bracket base 18 may have a contoured profile that corresponds to the curved contour of the patient's tooth surface to which the bracket base 18 is bonded and may carry optional structure (not shown), such as a bond pad, for enhancing the strength of the adhesive bond with the patient's tooth surface.

The bracket body 12 includes a pair of sidewalls 20, 22 that are substantially parallel to each other and that are oriented generally in gingival-occlusal planes when the bracket base 18 is secured to the tooth. Bracket body 12 also includes a pair of sidewalls 24, 26 that are substantially parallel to each other and that are oriented generally in mesial-distal planes when the bracket base 18 is secured to the tooth. Respective pairs of the sidewalls 20, 22, 24, 26 converge to define bracket body corners, which may be chamfered or curved.

The bracket body 12 includes an integral body extension 28 that projects outwardly beyond sidewall 24 in either an occlusal or gingival direction when the bracket base 18 is secured to the tooth. The bracket body 12 includes another body extension 30 that projects beyond the opposite sidewall 26 in the opposite direction to the body extension 28. The body extensions 28, 30 may define tie wings providing attachment points to, for example, apply torsional forces to the tooth to which the orthodontic bracket 10 is attached or if the tooth is severely malpositioned during the initial treatment stages. Body extension 28, which is roughly centered between the sidewalls 20, 22 of the bracket body 12, includes opposite sidewalls 29, 31.

An archwire slot 32 is bounded by two side surfaces 34, 36 and a base surface 38 that penetrate through the sidewalls 20, 22 to define a channel that extends across the bracket 10 generally in the mesial-distal direction. The base surface 38 joins the side surfaces 34, 36 and the distance between the side surfaces 34, 36 determines the physical dimensions of archwires that can be inserted into the archwire slot 32. The archwire slot 32 defines a channel that receives an archwire 33 for transferring a corrective force from the archwire 33 to the bracket 10, which coerces movement of the tooth to which the bracket 10 is secured relative to nearby teeth in the patient's mouth. The channel defined by the archwire slot 32 opens toward either the cheek or lips contingent upon the location within the upper or lower jaw of the tooth to which the bracket 10 is attached. When the latching member 14 is in the opened position (FIG. 5), the archwire slot 32 is accessible for inserting and removing the archwire 33. When the latching member 14 is in the closed position (FIG. 1), the archwire 33 is secured in the archwire slot 32 to ligate the archwire 33 to the bracket 10.

The latching member 14 includes a main body 40 and arms 48, 50 projecting from one side edge 49 of the main body 40. The arms 48, 50 are separated by a clearance distance adequate to receive the body extension 28 when the latching member 14 is mounted to the bracket body 12. Recessed regions or lands 44, 46 are disposed adjacent to the opposite sidewalls 29, 31, respectively, of the body extension 30. The lands 44, 46 provide clearance space for the arms 48, 50 and movement of the arms 48, 50 as the latching member 14 is moved between the opened and closed positions.

With continued reference to FIGS. 1-5, arms 48, 50 are coupled with the hinge pin 16. The hinge pin 16 defines a pivot axis that operates as an axis of rotation 41 (FIG. 2) about which the latching member 14 is moved relative to the body extension 28. The axis of rotation 41 coincides with an axis of symmetry for the cylindrical shape of the hinge pin 16 in the representative embodiment of the bracket 10.

A passageway 42 extends in the mesial-distal direction through the bracket body 12 and includes opposite open ends that intersect the opposite sidewalls 29, 31 of the body extension 28. The hinge pin 16, which is longer than the length of the passageway 42, is disposed in the passageway 42. Opposite ends 52, 54 of the hinge pin 16 project outwardly from the respective opens ends of passageway 42. The passageway 42 is generally aligned with the axis of rotation 41.

Arm 48 of latching member 14 includes an opening 56 that receives one projecting end 52 of the hinge pin 16. Arm 50 of latching member 14 includes an opening 58 that receives the other projecting end 54 of the hinge pin 16. In the representative embodiment, the openings 56, 58 are cylindrical bores penetrating through the respective one of the arms 48, 50. Each of these engagements, which physically secure the latching member 14 to the bracket body 12, includes sufficient clearance to permit free pivoting motion of the latching member 14 relative to the bracket body 12 along the axis of rotation 41.

Figure 2:
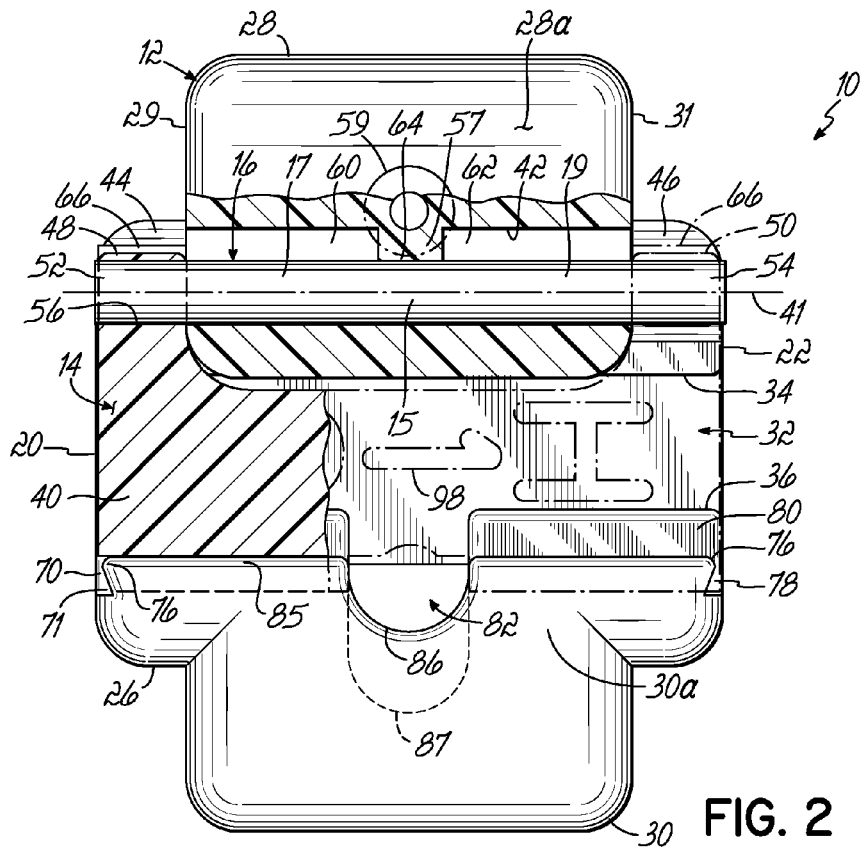
FIG. 2 is a front view in partial cross-section of the orthodontic bracket of FIG. 1.

As best shown in FIG. 2, the passageway 42 has two tubular chambers or regions 60, 62 that collectively extend along the majority of the length of the passageway 42. The tubular regions 60, 62 intersect the respective sidewalls 29, 31 of the body extension 28. The bracket body 12 and latching member 14 are arranged such that tubular region 60 is juxtaposed with cylindrical opening 56 and tubular region 62 is juxtaposed with cylindrical opening 58. In the representative embodiment, tubular regions 60, 62 each have an oval cross-sectional profile from a perspective viewed parallel to the axis of rotation 41 of the hinge pin 16. More specifically, the tubular regions 60, 62 in the representative embodiment are oval or slotted in shape with each consisting of two concave end surfaces connected by parallel planar surfaces and a major axis of the slot aligned substantially parallel to the non-collinear direction 90. When the bracket base 18 is secured to the tooth, the major axis of each of the tubular regions 60, 62 is oriented substantially in the gingival-occlusal direction and may be orthogonal to the axis of rotation 41.

A tubular chamber or region 64 of the passageway 42 is disposed centrally between the two tubular regions 60, 62. The tubular region 64 has a substantially cylindrical shape with a circular cross-sectional profile when viewed from a perspective parallel to the axis of rotation 41 of the hinge pin 16. A corresponding central region 15 of the hinge pin 16 is engaged with the tubular region 64 of passageway 42 to mechanically couple the latching member 14 with the bracket body 12. Tubular region 64 has a short axial length in comparison with the axial length of the tubular regions 60, 62 so that the hinge pin 16 is secured within the passageway 42 over a relatively short portion of its entire length. The central region 15 of the hinge pin 16 and the tubular region 64 of passageway 42 have a close tolerance fit that may be established by a staking process using a pointed tool that creates a tapered perforation 59 in the bracket body and causes the material of the bracket body 12 surrounding tubular region 64 to deform. The resulting deformation region 57 supplies the mechanical engagement between the bracket body 12 and the central region 15 of hinge pin 16 and constrains movement of the central region 15 of hinge pin 16 relative to the bracket body 12.

A first intermediate region 17 of the hinge pin 16, which is disposed along the axial length of the hinge pin 16 between the projecting end 52 and the secured central region 15, is positioned in tubular region 60. A second intermediate region 19 of the hinge pin 16, which is disposed along the axial length of the hinge pin 16 between the projecting end 54 and the secured central region 15, is positioned in the other tubular region 62. The tubular regions 60, 62, which have a larger cross sectional area when viewed along the axis of rotation 41 than the central tubular region 64, provide clearance or relief spaces for the flexing of the intermediate portions 17, 19 of the hinge pin 16.

The tubular regions 60, 62 may be shaped to allow bidirectional flexing of the hinge pin 16 in substantially one plane bounded between the opposite concave end surfaces of tubular regions 60, 62 and constrained by the planar surfaces of regions 60, 62 between the concave end surfaces, or may be alternatively shaped to permit flexing in a multitude of directions. This permits the intermediate regions 17, 19 of the hinge pin 16 and the latching member 14 to move in a direction generally indicated by single headed arrow 90 that is not collinear with the axis of rotation 41. In one embodiment, the non-collinear direction 90 is oriented to be perpendicular to the axis of rotation 41.

This alternative bidirectional design gives the hinge pin 16 the room needed for flexing when the latching member 14 is near the closed position, but restricts movement when the latching member is in other positions, such as the opened position or any position between the opened and closed positions. Limiting the movement of the hinge pin 16, for example, in the labial/lingual direction may enhance control over the archwire 33 because the latching member 14 is constrained by the hinge pin 16 in the labial/lingual direction.

Arm 48 of the latching member 14 includes an optional detent 66 defined as an outwardly-projecting ridge that bulges outwardly and interrupts an otherwise smoothly curved surface. Similarly, arm 50 of the latching member 14 includes an optional detent 68 also defined as an outwardly-projecting ridge that interrupts an otherwise smoothly curved surface. The detents 66, 68, which are aligned generally parallel to the axis of rotation 41, cooperate to hold the latching member 14 in the opened position (FIGS. 5, 6) by engaging a portion of a corresponding one of the lands 44, 46. The resistance provided by this engagement is selected to be adequate to prevent inadvertent closing by a force applied to the latching member 14, when the latching member 14 is in the opened position, that is below a certain threshold magnitude. The resistance provided by the detents 66, 68 is selected to be easily overcome by application of a pivoting force about the axis of rotation 41 that is greater than the threshold magnitude for movement and directed to pivot the latching member 14 from the opened position toward the closed position.

The archwire slot 32 has an entrance opening defined between side surfaces 34, 36. Body extension 30 has a labial surface 30a covering a labial side of the bracket body 12 and the body extension 28 has a labial surface 28a covering another labial side of the bracket body 12 that is separated from labial surface 30a by the access opening of the archwire slot 32. For purposes of description, the labial sides of the bracket body 12 may be considered to be divided at a boundary extending through a center plane of the archwire slot 32.

With continued reference to FIGS. 1-5, the main body 40 of latching member 14 has a rear surface 69 that closes the access opening into the archwire slot 32 and confronts the archwire 33 when the latching member 14 is in the closed position. The main body 40 also includes a front surface 67 that faces away from the archwire slot 32 and bonding base 18, when the latching member 14 is in the closed position, and toward the cheek or lips, when the bracket 10 is mounted to a tooth. The main body 40 of the latching member 14 includes a side edge 71 that is opposite to side edge 49 of the main body 40 from which the arms 48, 50 project and opposite side edges 61, 63 that connect side edges 49, 71. The arms 48, 50 curve slightly inwardly relative to the rear surface 69 of the main body 40 toward the lands 44, 46. The arms 48, 50 and the lands 44, 46 have complementary curvatures.

The orthodontic bracket 10 includes a latch mechanism that relies on cooperation between the hinge pin 16 and structures formed on the bracket body 12 and the main body 40 of the latching member 14, as described below, to secure the closed latching member 14 with the bracket body 12. Extending laterally along width, w, of the main body 40 at a location between the side edge 71 and the front surface 67 is a locking lip 72. The locking lip 72 includes a locking surface 79 and a contoured surface 70 that joins the surface 79 of locking lip 72 with the front surface 67. Surface 79 of locking lip 72 and contoured surface 70 bound two sides of a groove that also extends laterally along the width, w, of the main body 40. When the latching member 14 is mounted to the bracket body 12 and pivoted to the closed position, the locking lip 72 and side edge 71 are located proximate to the body extension 30 with the side edge 71 having a confronting relationship with the body extension 30.

Figure 3:
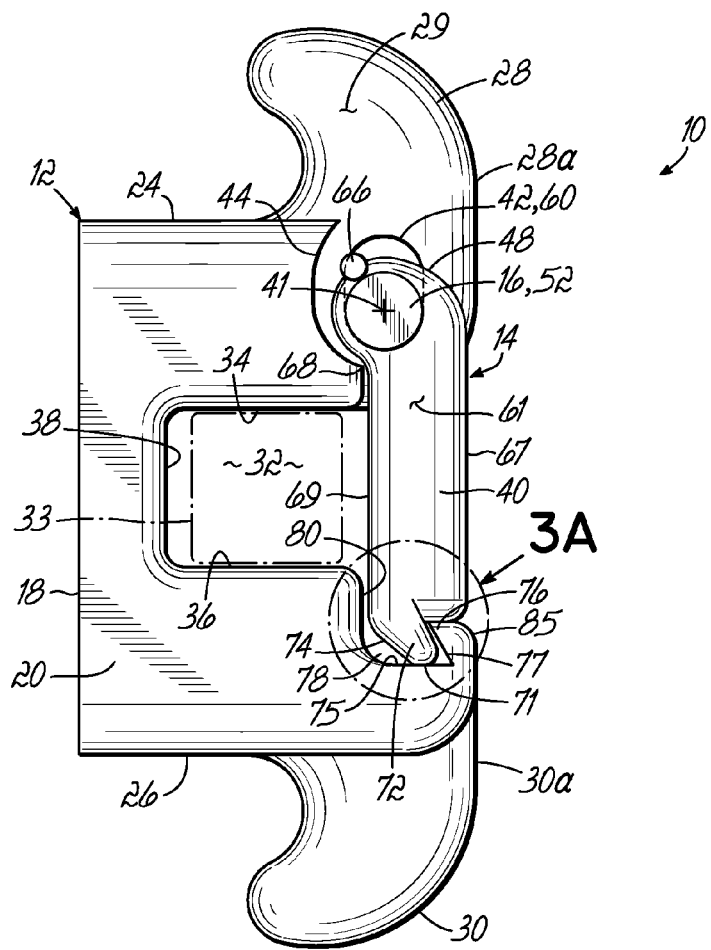
FIG. 3 is a side view of the orthodontic bracket of FIGS. 1 and 2.
Figure 3A:
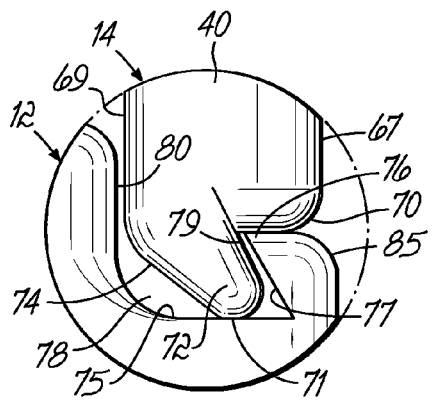
FIG. 3A is an enlarged view of an encircled portion of FIG. 3.

A chamfered surface 74 is defined on the main body 40 between the rear surface 69 and the side edge 71. The chamfered surface 74, which is inclined at a shallow angle relative to the rear surface 69, is beneficial for use in latching the latching member 14 in the closed position, as described in greater detail below and as best shown in FIGS. 3 and 3A. The side edge 71, locking lip 72, and chamfered surface 74 extend along the main body 40 with a fixed spatial relationship and are generally aligned with the axis of rotation 41. The side edge 71, locking surface 79 of locking lip 72, and chamfered surface 74 also connect the rear and front surfaces 67, 69 of the main body 40. In the illustrated embodiment, the main body 40 has a substantially uniform thickness so that the separation between the rear and front surfaces 67, 69 is independent of location on the main body 40 and so that the rear and front surfaces 67, 69 are contained in substantially parallel planes.

The body extension 30 includes an undercut region or recess 78 defined between an inclined surface 77 of a ledge or lip 76 and a shoulder 80 formed in the bracket body 12. A surface 75 joins surface 77 with shoulder 80. The inclined surface 77 of lip 76 confronts the surface 79 of lip 76, which is also inclined. The surfaces 77, 79 are inclined at approximately equal inclination angles. The recess 78 is located on opposite side of the bracket body 12 from the passageway 42. The recess 78 opens generally in the non-collinear direction 90.

The shoulder 80 adjoins side surface 36 of the archwire slot 32 along a tight radius corner. A contoured surface 85 is defined where the labial surface 30a of the body extension 30 intersects the entrance to archwire slot 32. The lip 76 and shoulder 80 are separated by a distance that permits the locking lip 72 to be placed in the recess 78 when the latching member 14 is closed and latched. In the closed position with the lips 72, 76 engaged, forces transferred from the archwire 33 to the bracket body 12 will not disengage the latching member 14 from its locked condition.

When the latching member 14 is closed, the hinge pin 16 locates the latching member 14 relative to the bracket body 12 such that the end of the latching member 14 carrying the lip 72 toward the locked position so that the lips 72, 76 are confronting and mutually engaged. The recess 78 has a depth measured between surface 75 and the location where surface 77 meets contoured surface 85. The depth of the recess 78 and the flexibility of the material forming the hinge pin 16 are selected such that the latching member 14 can be moved a distance in the non-collinear direction 90 adequate to engage the lip 72 with the recess 78 to place the latching member 14 in the closed position and to disengage the lip 72 from the recess 78 to release the latching member 14 from the closed position. The lips 72, 76 have an interlocking relationship in the closed position, although the invention is not so limited. For example, lip 76 in the body extension 30 may be modified so that the lips 72, 76 (and lip 72 and recess 78) do not exhibit an interlocking relationship when the latching member 14 is closed, as depicted in an alternative embodiment shown in FIG. 12.

The inclined surfaces 77, 79 contact each other when the latching member 14 is in the closed position such that the lip 76 of the latching member 14 is interlocked with the recess 78 of the bracket body 12. In the representative embodiment, surface 79 on lip 72 and surface 77 on lip 76 are substantially flat or planar with complementary inclination angles so that the lips 72, 76 interlock to provide additional resistance against movement of the latching member 14 relative to the bracket body 12. However, the invention is not so limited. When the latching member 14 is moved in the non-collinear direction 90, the hinge pin 16 applies a spring bias that resists the movement.

The lips 72, 76 have an interlocking relationship, although the invention is not so limited. For example, lip 76 in the body extension 30 may be modified so that the lips 72, 76 do not exhibit an interlocking relationship when the latching member 14 is closed, as depicted in an alternative embodiment shown in FIG. 12 and as described below.

Figure 3B:
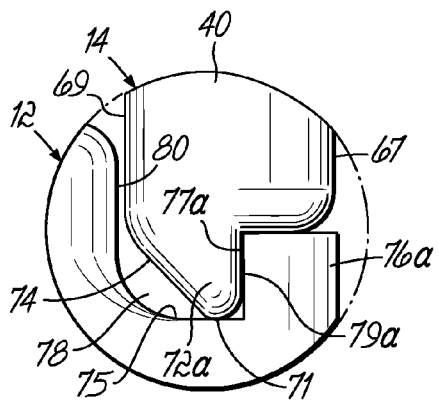
FIG. 3B is an enlarged view similar to FIG. 3A of an orthodontic bracket in accordance with an alternative embodiment of the invention.
Figure 4:
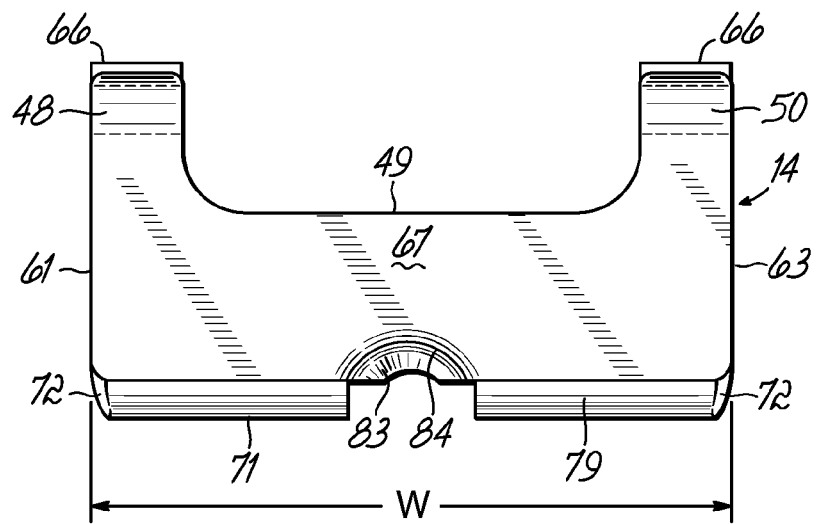
FIG. 4 is a front view of a latching member of the orthodontic bracket of FIGS. 1-3.

In an alternative embodiment and as shown in FIG. 3B, the latch mechanism of bracket body 12 and latching member 14 may be modified to change the configuration of the latch mechanism. Specifically, the lip of latching member 14 includes a surface 72a that is connected by contoured surface 70 with the front surface 67. The body extension 30 includes a ledge or lip 76a, which is similar to locking lip 76, having a surface 77a that overhangs the recess 78. In this alternative embodiment, surfaces 72a, 77a are not inclined relative to each other so that the latch mechanism is not interlocking.

With renewed reference to FIGS. 1-5, the orthodontic bracket 10 includes a round tool hole or opening, generally indicated by reference numeral 82, that is exposed from the labial/buccal direction when the bracket base 18 is bonded with the patient's tooth surface. The tool opening 82 is defined partially by a concave region 84 defined along the side edge 71 of latching member 14 and partially by a concave region 86 defined on a side edge of the body extension 30 that faces the archwire slot 32. When the latching member 14 is in the closed position, the concave regions 84, 86 are confronting and registered relative to each other to define the tool opening 82. Concave region 86 includes a curved sidewall 87 that extends into the bracket body 12 and concave region 84 has a curved sidewall 83 that penetrates through the latching member 14. The curved sidewalls 83, 87 are arranged about a central axis that is inclined relative to the plane of the bonding base 18.

In the representative embodiment, the locking lips 72, 76 are depicted as complementary flat surfaces, although the invention is not so limited. In the representative embodiment of the latching member 14, the continuity of the contoured surface 70, side edge 71, and locking lip 72 is interrupted by the concave region 84. However, the lateral extent or length of the contoured surface 70, side edge 71, and locking lip 72 along the width, w, of the main body 40 and between side edges 61, 63 is a design parameter determined according to, for example, the application for the bracket 10. The contoured surface 70, side edge 71, and locking lip 72 may be shorter than shown in the representative embodiment, may begin at a location along the width, w, of the main body 40 other than proximate to the side edges 61, 63, may end at a location along the width, w, of the main body 40 other than proximate to the concave region 84, and may have asymmetrical lengths and locations.

As shown in FIG. 1, the latching member 14 may be opened using an instrument 91 with a tip 92 dimensioned to be inserted into the circular tool opening 82. The instrument 91 is manually held by the clinician using a grip portion (not shown). The tool opening 82 may be slightly angled as shown in the representative embodiment or, in an alternative embodiment, may be vertically oriented. Angling the tool opening 82 may place the instrument 91 at a more comfortable angle for use by the clinician.

In an alternative embodiment of the invention, a small dimensional clearance may be provided between the rear surface 69 of the latching member 14 and the shoulder 80 formed in the bracket body 12. When the latching member 14 is in the closed position, the dimensional clearance may be advantageous for changing the distance between the rear surface 69 of the latching member 14 and the base surface 38 of the archwire slot 32. This effectively decreases the height of the archwire slot 32 by changing the clearance between the rear surface 69 and the archwire 33. The change is implemented by mounting a ligature in the form of an elastomeric O-ring to the bracket 10 about one of the body extensions 28, 30 in a manner that applies a force to the latching member 14 directed toward the base surface 38 of the archwire slot 32. This feature may be beneficial when a clinician is finishing an orthodontic treatment and provides the clinician with an additional degree of flexibility.

An identification marking 98 (FIGS. 2 and 8), which is preferably one or more alphanumeric characters and/or symbols, may be defined in the base slot surface 38 bounding the archwire slot 32. The optional identification marking 98 may be used as a visible indicator to the clinician that denotes bracket location and permits the clinician to distinguish between high and low torque brackets 10. In the latter regard, one such system includes inscribing an "H" as one of the alphanumeric characters to identify a high torque bracket 10 or an "L" as one of the alphanumeric characters to identify a low torque bracket 10. Conventional techniques for forming the identification marking 98, which are known to persons having ordinary skill in the art, may apply the identification marking 98 either during the fabrication of the bracket body 12 or after the bracket body 12 is fabricated.

Figure 5:
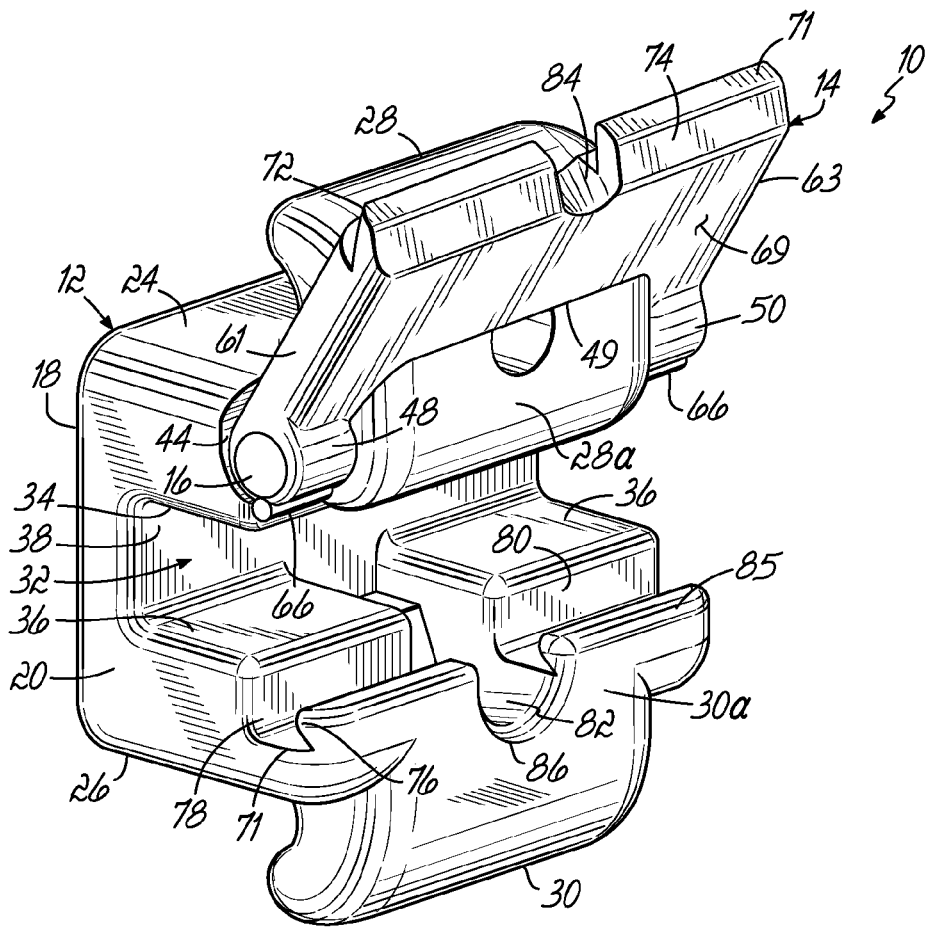
FIG. 5 is a perspective view similar to FIG. 1 in which the ligating member of the orthodontic bracket is shown pivoted to an opened position.
Figure 6:
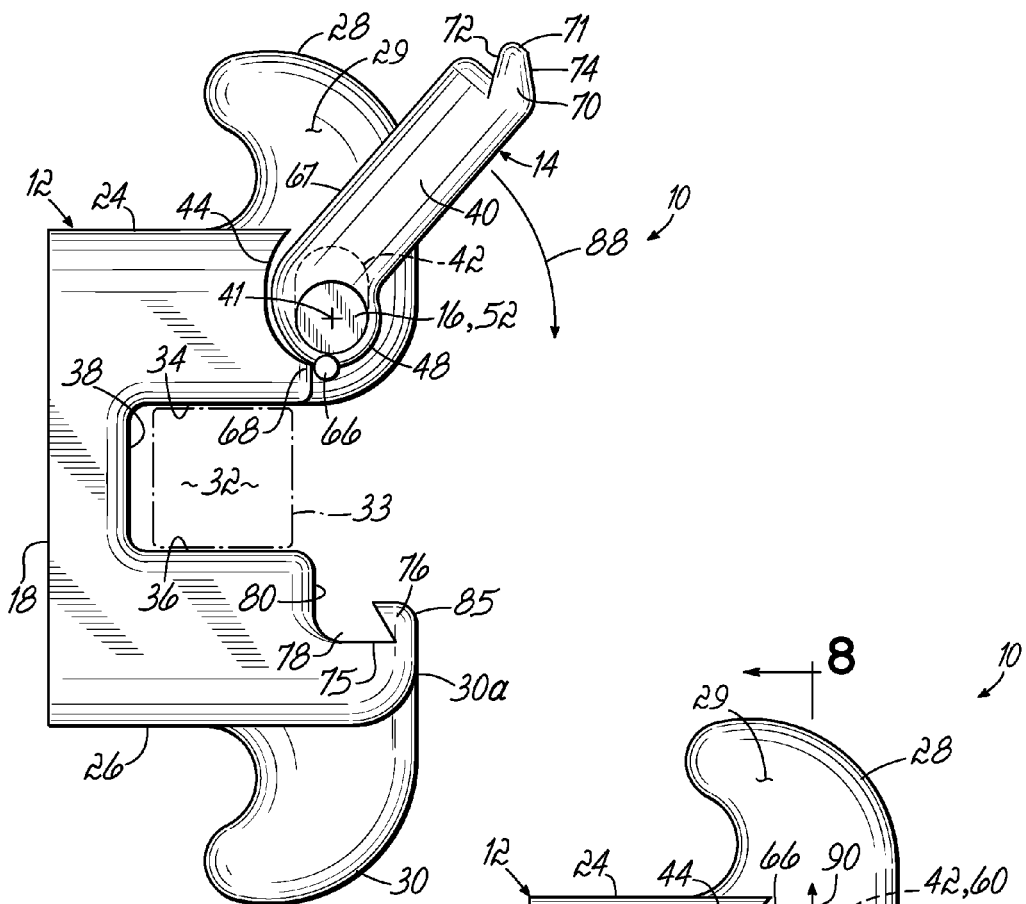
FIG. 6 is a side view of the orthodontic bracket of FIG. 5.

In use and with reference to FIGS. 1-8, the orthodontic bracket 10 is typically applied to the patient's teeth as part of a set of similar brackets 10. The bracket base 18 on the bracket body 12 is mounted to the buccolabial surface of a tooth (not shown). At the time of mounting, the latching member 14 is initially in the opened condition, as shown in FIGS. 5 and 6. The archwire 33 is installed in the archwire slot 32. The latching member 14 is pivoted about the axis of rotation 41 along hinge pin 16 toward the body extension 28, as indicated by single headed arrow 88 (FIG. 6).

Figure 7:
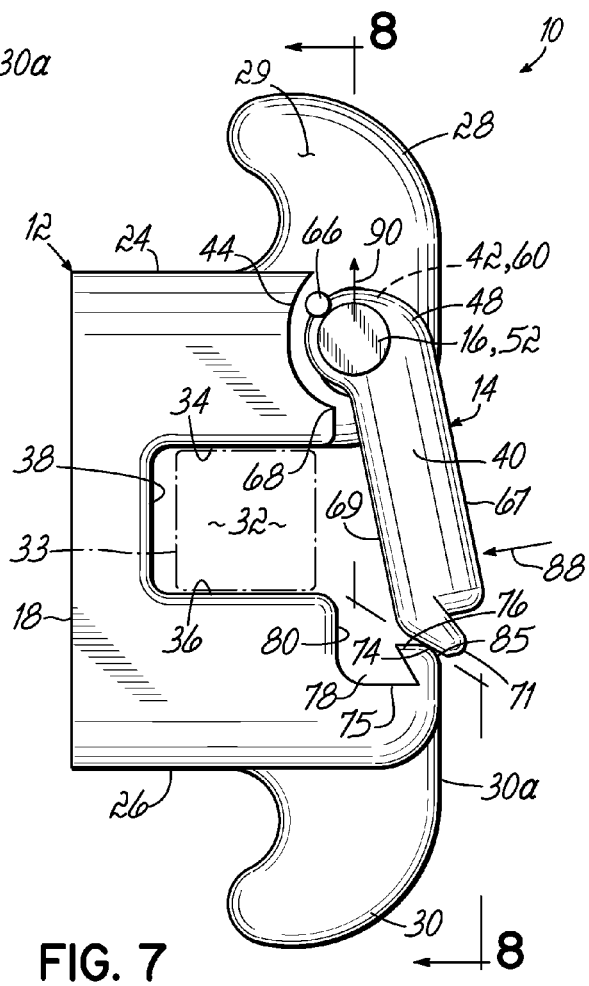
FIG. 7 is a side view of the orthodontic bracket similar to FIG. 6 with the latching member pivoted to an intermediate position between the opened and closed positions.
Figure 8:
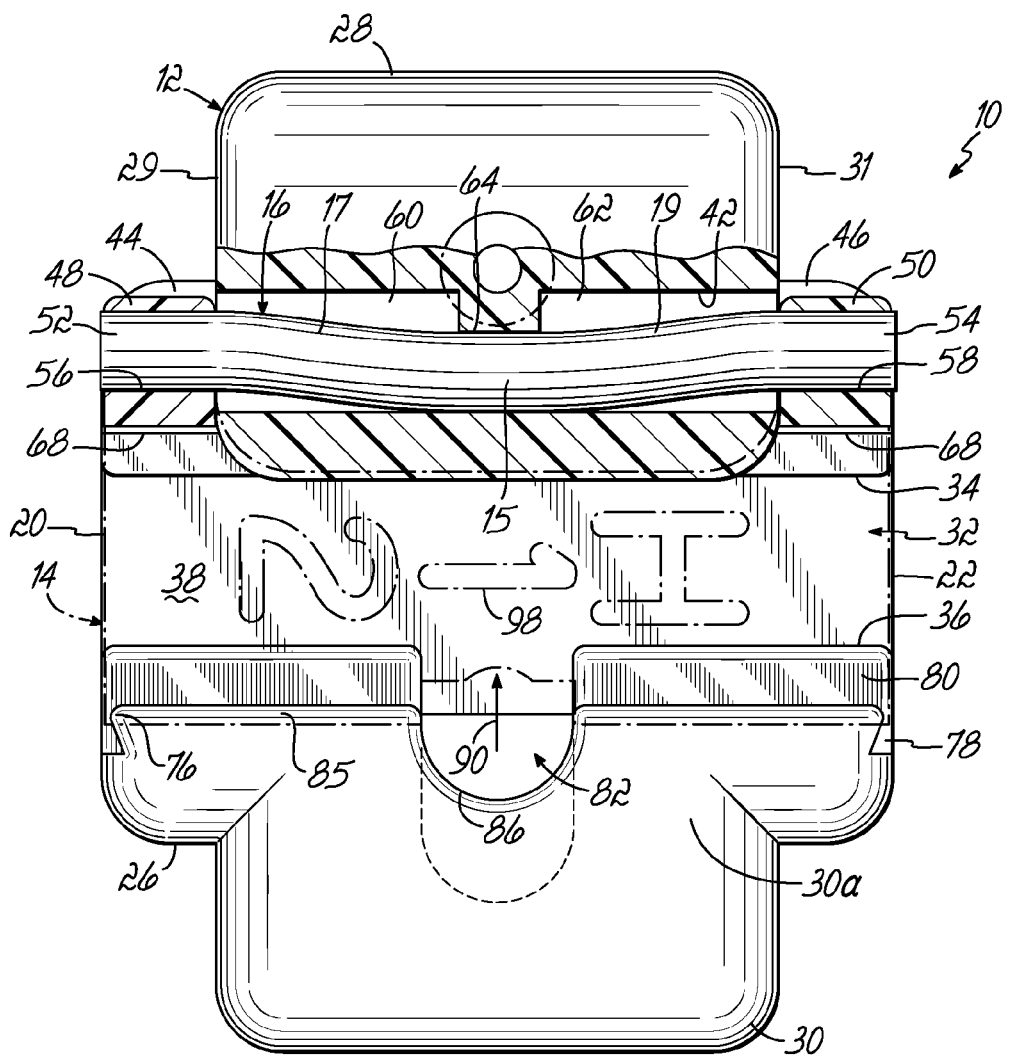
FIG. 8 is a cross-sectional view taken generally along line 8-8 in FIG. 7.

As the latching member 14 is pivoted, the chamfered surface 74 on the latching member 14 eventually physically contacts contoured surface 85 on the body extension 30. As shown in FIGS. 7 and 8, a force is applied to the latching member 14 in a direction generally indicated by single headed arrow 88 that is sufficient to place the latching member 14 in the closed position. Cooperation between the applied force 88 and the physical contact creates a camming action that moves the latching member 14 in the non-collinear direction 90 against an increasing spring bias applied by the hinge pin 16. This camming action provides a mechanical advantage that permits the latching member 14 to be closed and latched, if the clinician desires, without the assistance of a special tool or instrument.

The central region 15 of the hinge pin 16 has a fixed relationship with the central region 64 of the passageway 42. Under the influence of the applied force 88, the intermediate regions 17, 19 of the hinge pin 16 flex or move in the non-collinear direction 90 within the relief spaces defined by the tubular regions 60, 62, as evident from a comparison of FIGS. 2 and 8. Specifically, the tubular regions 60, 62 provide clearance for resilient deflection of the intermediate regions 17, 19 of the hinge pin 16 to flex in the non-collinear direction 90.

The material forming the hinge pin 16 has sufficient flexibility to permit flexing in the non-collinear direction 90 to an extent sufficient to permit the locking lip 72 on the latching member 14 to clear the lip 76 on the body extension 30. Direction 90 is non-collinear relative to the axis of rotation 41. The central region 15 of the hinge pin 16 is secured in the tubular region 64 against movement in the non-collinear direction 90 so that the intermediate regions 17, 19 of the hinge pin 16 can move in the respective tubular regions 60, 62.

When locking lip 72 clears lip 76, the spring bias applied to the latching member 14 by the hinge pin 16 forces the latching member 14 to move in the occlusal-gingival direction (i.e., in a direction opposite to the non-collinear direction 90). The directional spring bias urges the end of the latching member 14 carrying the locking lip 72 toward the locked and closed position so that the lips 72, 76 are confronting and mutually engaged. When the hinge pin 16 is subsequently moved by an applied force in the non-collinear direction 90 to open or close the latching member 14, the spring bias applied to the latching member 14 increases and opposes the movement in direction 90. In particular, the increase in the spring bias applied to the latching member 14 by the hinge pin 16 resists inadvertent opening of the closed latching member 14 and exerts a constant force that acts to maintain the latching member 14 in the closed position with the lip 72 secured in the recess 78.

In the closed position (FIG. 3), a significant portion of the main body 40 of the latching member 14 overlies the side surfaces 34, 36 and base surface 38 of the archwire slot 32. The archwire 33 positioned in the archwire slot 32 is blocked against removal by movement in a direction normal to the base surface 38 by the rear surface 69 of the latching member 14. The archwire 33 is trapped against movement in the occlusal-gingival direction by the side surfaces 34, 36. In this self-ligating manner, closing the latching member 14 ligates the archwire 33 to the bracket 10. No additional loose ligatures are required to retain the archwire 33 in the archwire slot 32.

Figure 9A:
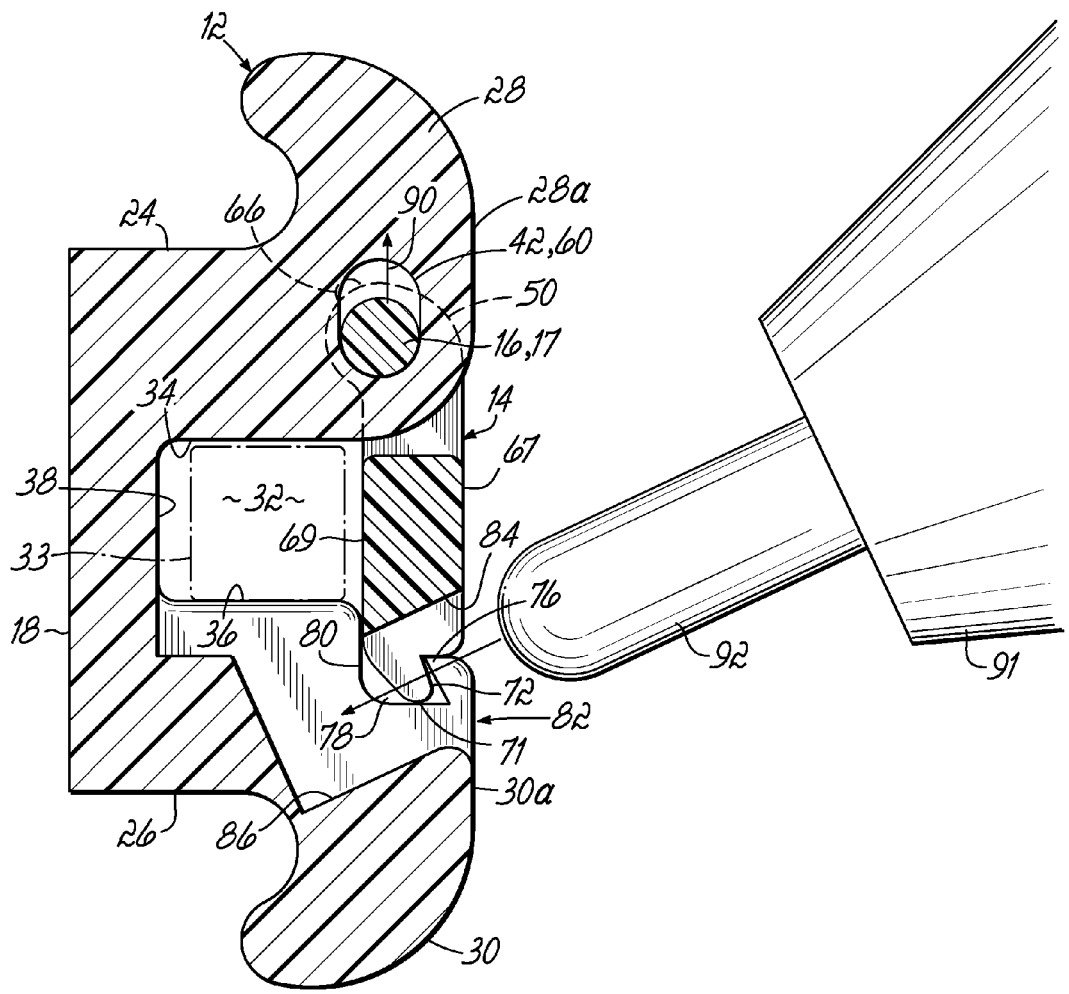
FIGS. 9A-C are a series of side views of the orthodontic bracket of FIGS. 1-8 illustrating the process for opening the latching member.
Figure 9B:
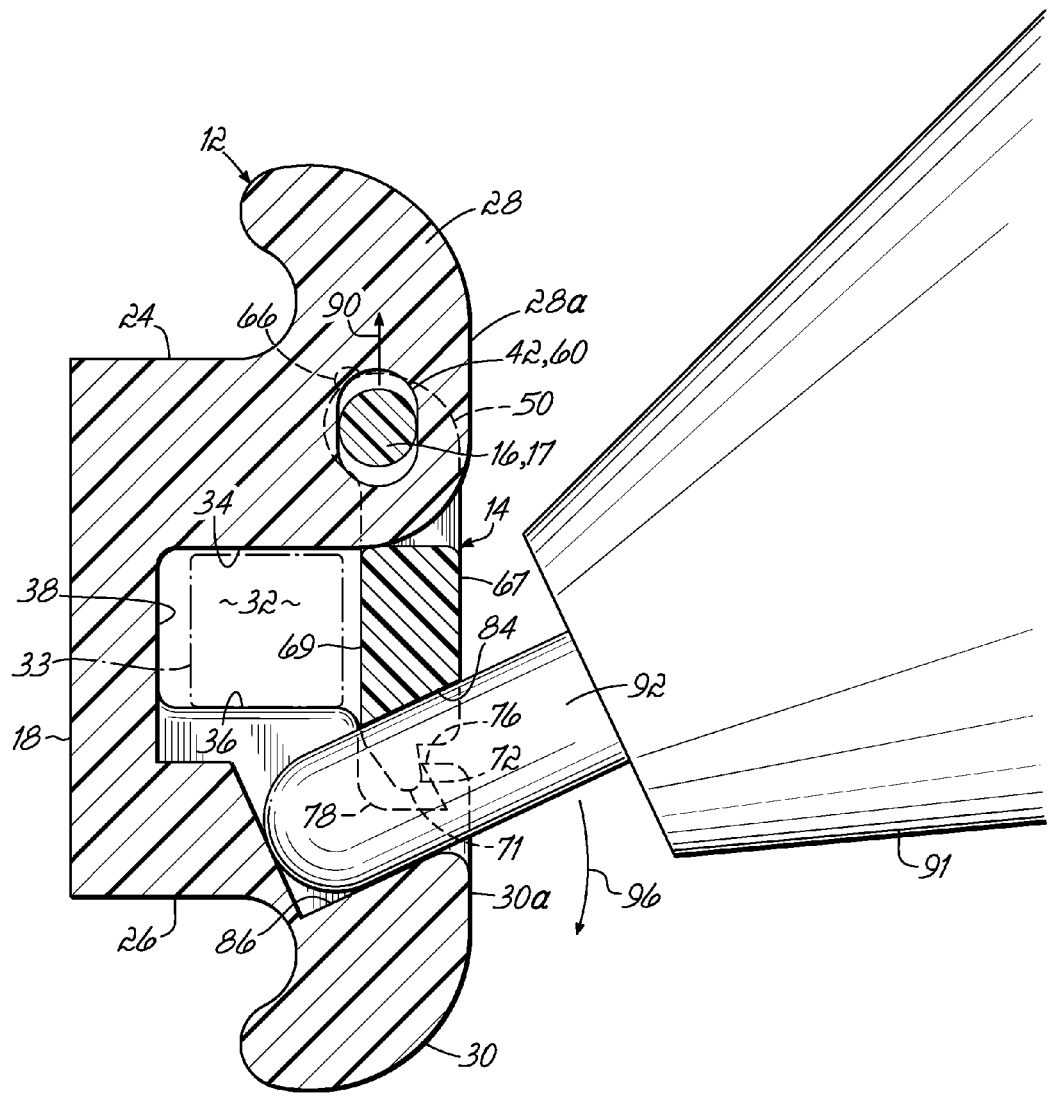
Figure 9C:
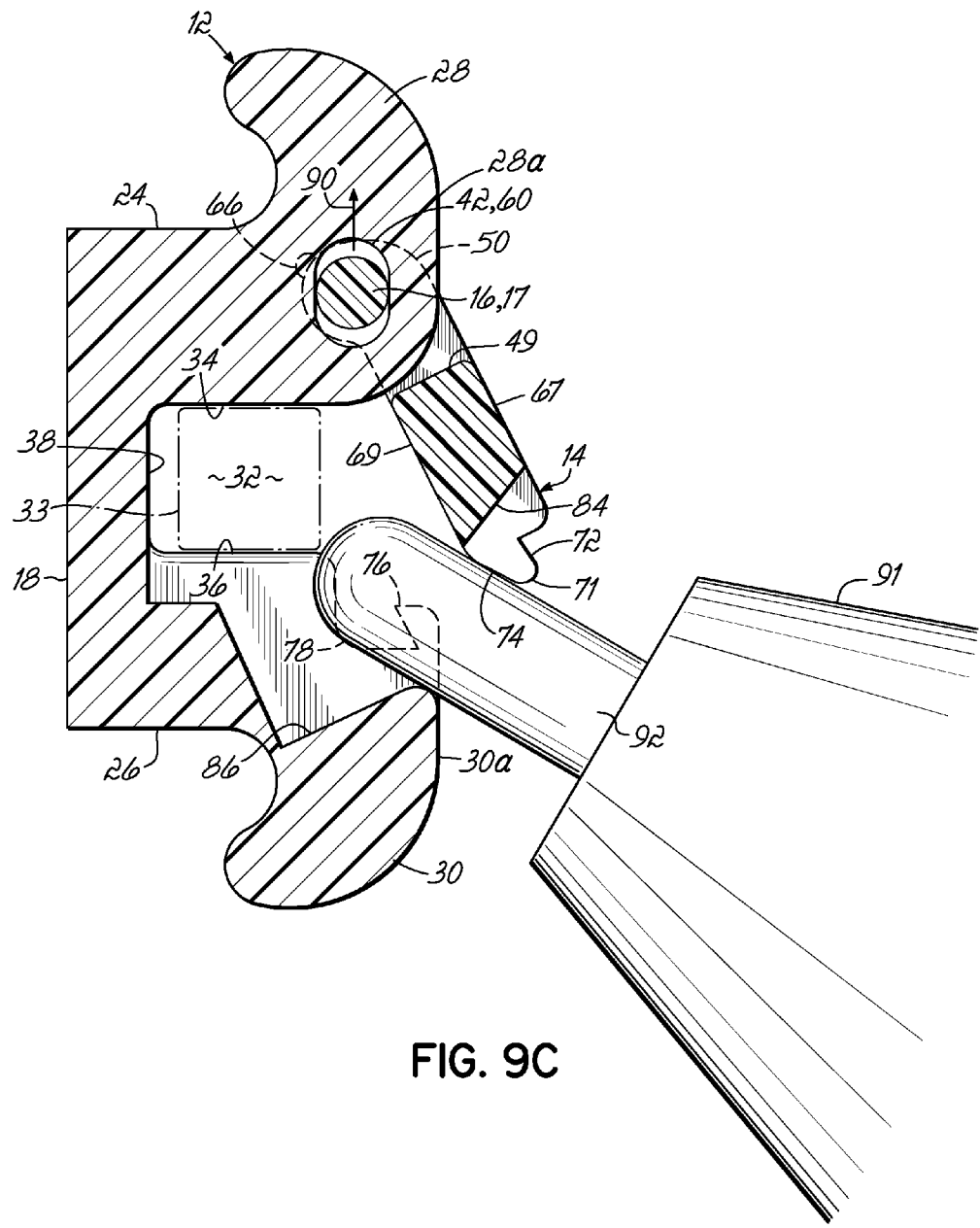

A procedure for opening the latching member 14 from its closed position to remove the archwire 33 from the archwire slot 32 may be described with specific references to FIGS. 9A-C. As best shown in FIG. 9A, the clinician maneuvers the instrument 91 to insert the tip 92 in the circular opening 82. As best shown in FIG. 9B, the instrument 91 uses the body extension 30 of bracket body 12 as a fulcrum point for moving the latching member 14 in a direction 96 generally opposed to the spring bias applied by the hinge pin 16 and generally collinear with the non-collinear direction 90. This causes the intermediate regions 17, 19 of the hinge pin 16 to freely flex in the oval regions 60, 62 of the passageway 42.

When the lip 72 carried on the latching member 14 clears the edge of lip 76 on the body extension 30 of bracket body 12, the instrument 91 is manipulated to pivot the front side edge 71 of the latching member 14 upward so that, when the tip 92 is removed, the action of the spring bias does not reengage the lips 72, 76. The latching member 14 is released to be pivoted about the axis of rotation 41 toward the opened position. In the opened position, the optional detents 66, 68 may secure the latching member 14 against inadvertently closing.

Figure 10:
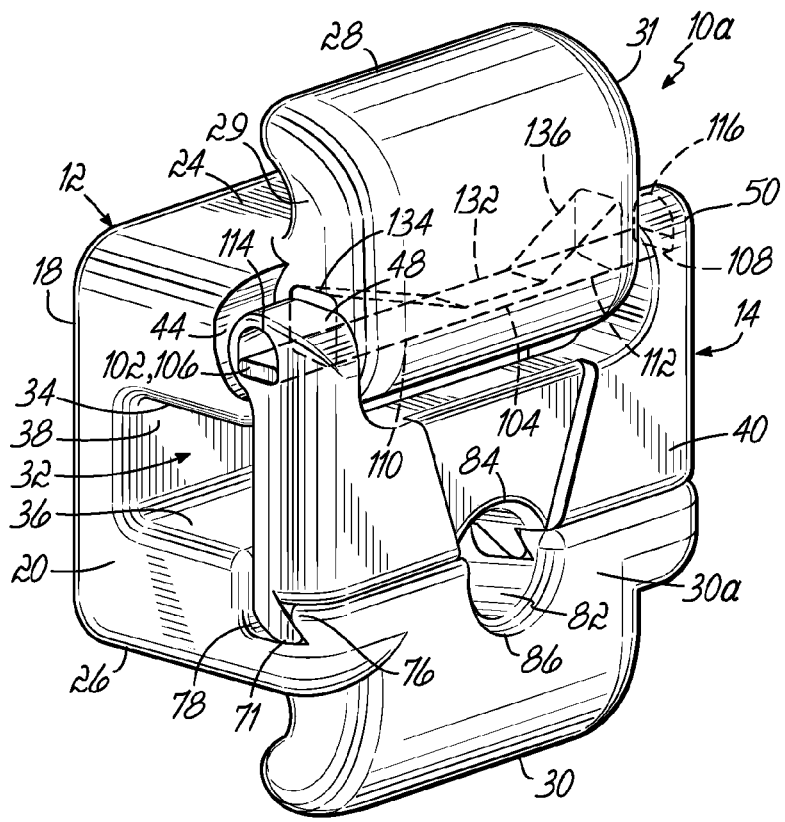
FIG. 10 is a perspective view of an alternative embodiment of the invention.
Figure 10A:
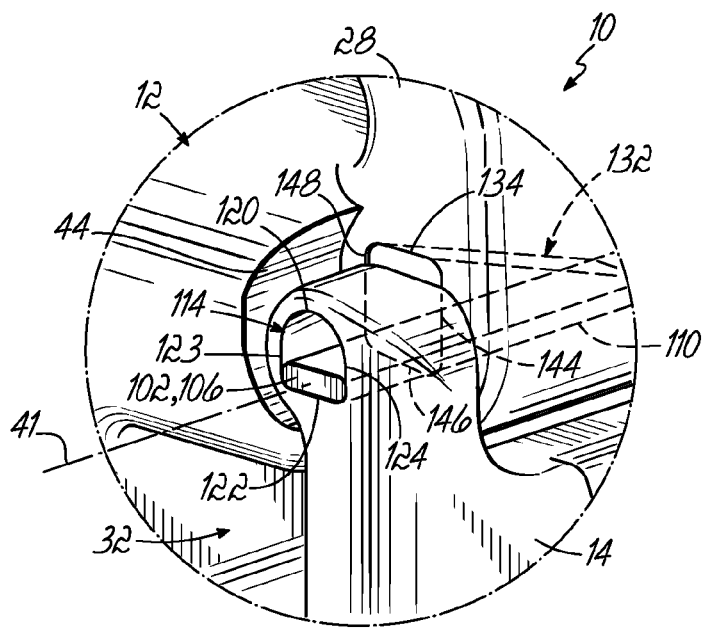
FIG. 10A is an enlarged view of a portion of FIG. 10.
Figure 11:
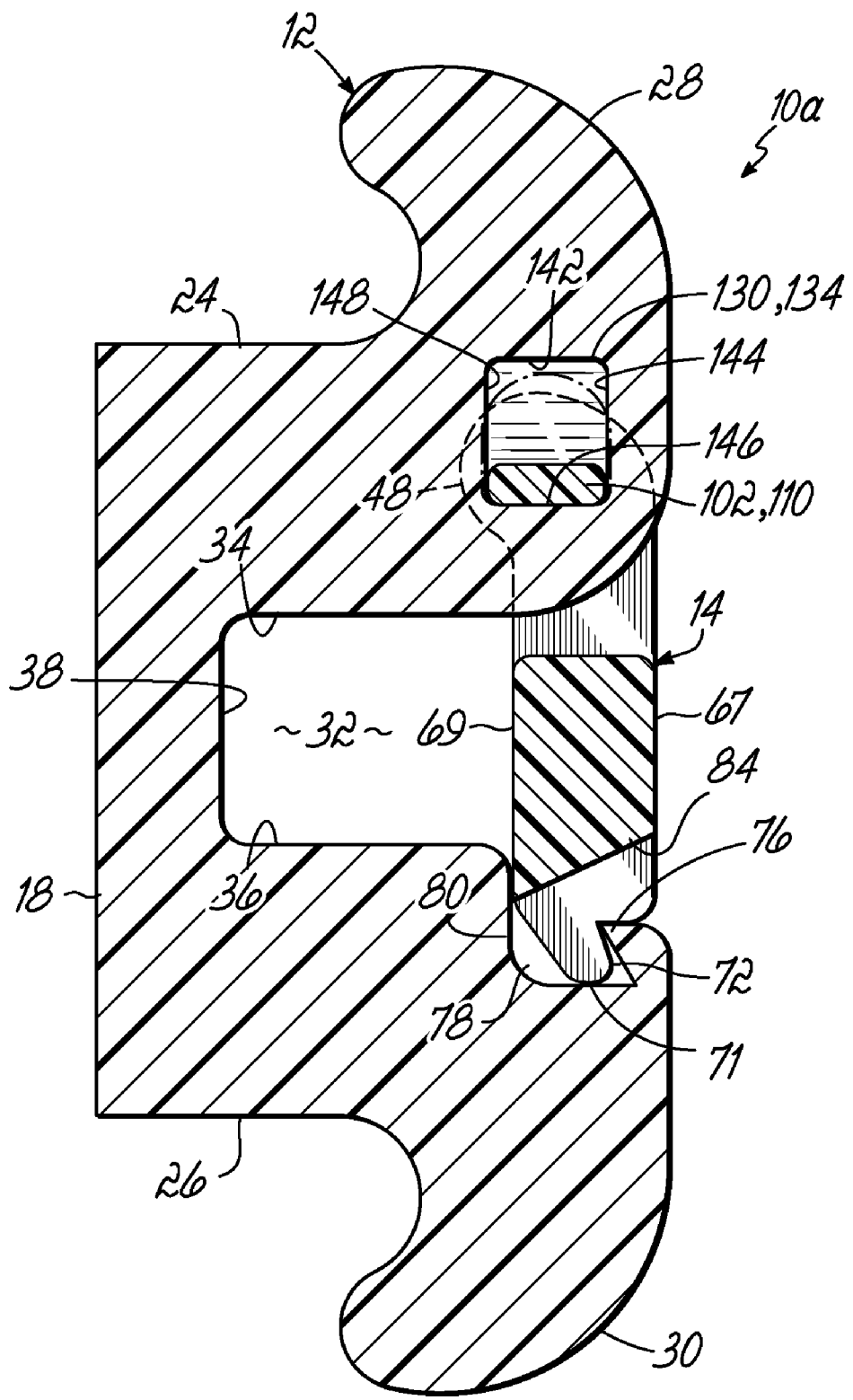
FIG. 11 is a cross-sectional view taken generally along line 11-11 in FIG. 10.

With reference to FIGS. 10, 10A, and 11 in which like reference numerals refer to like features in FIGS. 1-9 and in accordance with an alternative embodiment, an orthodontic bracket 10a may include a hinge pin 102 having a non-circular profile in cross section when viewed along an axis of rotation 41. In one specific embodiment, the hinge pin 102 may have a non-cylindrical, cross-sectional profile, when viewed along the axis of rotation 41, that is rectangular. The hinge pin 102 includes a rectangular central region 104 analogous to central region 15 (FIGS. 1-9) of hinge pin 16, rectangular opposite ends 106, 108 analogous to the opposite ends 52, 54 of the hinge pin 16 (FIGS. 1-9), and rectangular intermediate regions 110, 112 analogous to the intermediate regions 17, 19 of hinge pin 16 (FIGS. 1-9). Intermediate region 110 is disposed along the axis of rotation 41 between central region 104 and end 106. Intermediate region 112 is disposed along the axis of rotation 41 between central region 104 and end 108.

Arm 48 of the latching member 14 has an opening 114 and arm 50 of the latching member has an opening 116. The openings 114, 116, which are analogous to cylindrical openings 56, 58 (FIGS. 1-9), are non-cylindrical and, in the representative embodiment, are D-shaped to provide clearance for the pivoting of the hinge pin 102 when the latching member 14 is moved between the opened and closed positions. The D-shape of each of the openings 114, 116 is defined by a curved portion 120, a linear portion 122, and intervening line segment portions 123, 124 connecting each opposite end of the curved portion 120 with respective opposite ends of the linear portion 122. The curved portion 120 may be semicircular, as shown in FIG. 10.

The body extension 28 of the bracket body 12 has a passageway 130 that is analogous to passageway 42 (FIGS. 1-9). Passageway 130 includes a tubular region 132 analogous to the tubular region 64 (FIGS. 1-9) of passageway 42 and tubular regions 134, 136 that flank the centrally-located tubular region 132. Tubular regions 134, 136 are analogous to tubular regions 60, 62 (FIGS. 1-9) of passageway 42. The tubular regions 132, 134, 136 of passageway 130, which are arranged along the axis of rotation 41, have a rectangular cross-section, when viewed along the axis of rotation 41. Tubular region 132 penetrates through sidewall 29 of the body extension 28 and tubular region 134 penetrates through sidewall 31 of the body extension 28.

The cross-sectional area of tubular region 132 of passageway 130 is approximately equal to the cross-sectional area of the central region 104 of hinge pin 102, which fixes the location of the central region 104 relative to the bracket body 12. Tubular region 134 of passageway 130 narrows in cross-sectional area from its intersection at an open end with sidewalls 29 to its merger with one of the opposite open ends of the centrally-located tubular region 132. Similarly, tubular region 136 of passageway 130 narrows in cross-sectional area from its intersection at an open end with sidewall 31 to its merger with the other of the opposite open ends of tubular region 132.

Tubular region 134 of passageway 130 is bounded by side surfaces 142, 144, 146, 148 in which adjacent pairs of the side surfaces 142, 144, 146, 148 converge at corners. In the representative embodiment, side surface 142 is inclined relative to the other bounding side surfaces 144, 146, 148 to provide the narrowing in cross-sectional area of region 142. Tubular region 136 is bounded by a similar set of side surfaces such that the description of tubular region 134 is understood to apply equally to apply to tubular region 134. The enlarged cross-sectional area of tubular regions 134, 136, in comparison with the cross-sectional area of the intermediate regions 110, 112 of hinge pin 102 at the same location along the axis of rotation 41, provides the relief spaces for the flexing of the intermediate regions 110, 112 of hinge pin 102, as described above with regard to tubular regions 60, 62 of passageway 42 (FIGS. 1-9). Side surfaces 142, 146 are aligned generally in a plane parallel to the plane of side surfaces 34, 36 of archwire slot 32.

When the latching member 14 is closed, the intermediate regions 110, 112 of hinge pin 102 are substantially aligned with the linear portion 122 of each of the openings 114, 116 and with the side surfaces 142, 146. This relative arrangement and orientation between the intermediate regions 110, 112 and the passageway 130 makes the latching member 14 fairly secure in the lingual-gingival direction because the side surfaces 144, 148 of each of the tubular regions 134, 136 limit motion of the intermediate regions 110, 112 in a direction parallel with side surfaces 144, 148. This blocked motion generally prevents the latching member 14 from moving labially under the influence of forces applied by the archwire 33. The spring bias applied to the latching member 14 by the hinge pin 102 resiliently biases the lip 72 into recess 78 in a direction opposite to the non-collinear direction 90 (FIGS. 7, 8). The minor dimension of the intermediate regions 110, 112 of hinge pin 102 is shorter than the distance between the side surfaces 142, 146 in each of tubular regions 134, 136, which allows room for the intermediate regions 110, 112 to flex when the latching member 14 is moved to open and close the bracket 10a.

Figure 12:
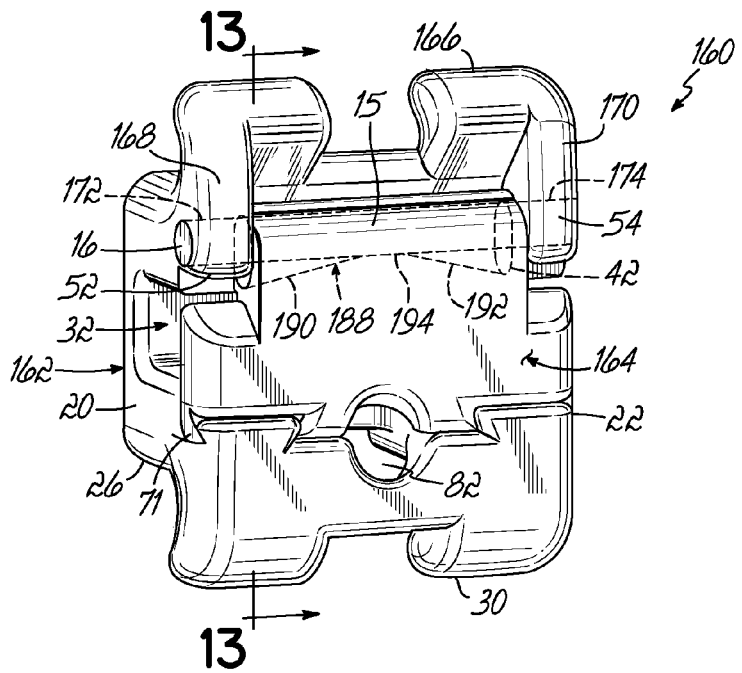
FIG. 12 is a perspective view of an alternative embodiment of the invention.
Figure 13:
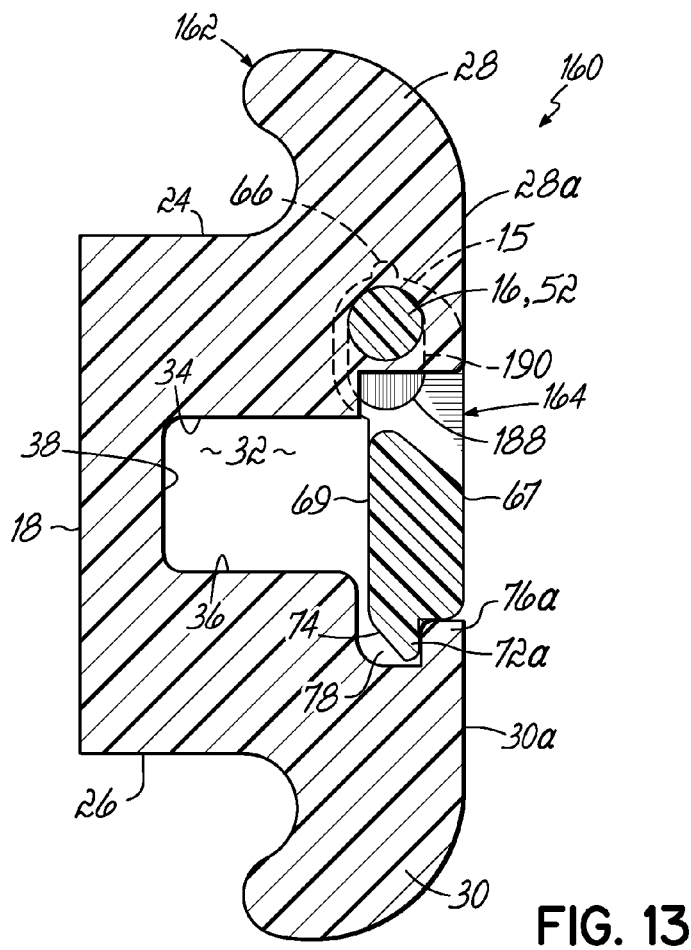
FIG. 13 is a cross-sectional view taken generally along line 13-13 in FIG. 12.

With reference to FIGS. 12 and 13 in which like reference numerals refer to like features in FIGS. 1-9 and in accordance with an alternative embodiment, an orthodontic bracket 160, which is otherwise identical to bracket 10, includes bracket body 162 and a latching member 164 that have been modified to situate the relief spaces (i.e., oval and circular cross section regions) for the hinge pin 16 in the latching member 164. To that end, a body extension 166 of the bracket body 162 includes a spaced-apart pair of supports 168, 170 positioned near the sidewalls 20, 22, respectively. Support 168 includes an opening 172 that is engaged with the projecting end 52 of the hinge pin 16. Support 170 includes an opening 174 that is engaged with projecting end 54 of the hinge pin 16. The multiple laterally-spaced pivot points defined by the engagement between the projecting ends 52, 54 of the hinge pin 16 and the openings 170, 172, respectively, for opening and closing the bracket 160, therefore, differ from the single central pivot point of bracket 10 (FIGS. 1-9). However, the operation and structure of the bracket 160 is substantially the same as for bracket 10, as is the method of using the bracket 160.

To that end, the latching member 164 includes a passageway 188 that is analogous in construction to passageway 42 in bracket body 12 (FIGS. 1-9). Along the majority of its length, the passageway 188 has tubular regions 190, 192 of relatively large cross-sectional area. The tubular regions 190, 192, which are similar in construction and function to tubular regions 60, 62 (FIGS. 1-9), are oriented with a major axis of the oval-shaped cross-sectional profile substantially aligned in the gingival-occlusal direction when the bracket base 18 is secured to the tooth. The intermediate regions 17, 19 of the hinge pin 16 reside in the tubular regions 190, 192. A tubular region 194 of the passageway 188, which is centrally disposed between tubular regions 190, 192, has a shape complementary to the shape of the hinge pin 16 and is connected with the central region 15 of hinge pin 16. As a result, the intermediate regions 17, 19 of the hinge pin 16 can resiliently deflect within the tubular regions 190, 192 of passageway 188 in the non-collinear direction 90 (FIGS. 7, 8) relative to the central region 15 of the hinge pin 16, which is secured against movement in the non-collinear direction 90 (FIGS. 7, 8).

While the invention has been illustrated by a description of various preferred embodiments and while these embodiments have been described in considerable detail in order to describe the best mode of practicing the invention, it is not the intention of applicant to restrict or in any way limit the scope of the appended claims to such detail. Additional advantages and modifications within the spirit and scope of the invention will readily appear to those skilled in the art.

The invention itself should only be defined by the appended claims, wherein I claim:

1. A method of using an orthodontic bracket having a bracket body and a latching member pivotally coupled with the bracket body for movement relative to the bracket body about an axis of rotation defined by a hinge pin coupling the latching member with the bracket body, the method comprising:

applying a spring bias to the latching member with the hinge pin;

securing a portion of the hinge pin against movement; and applying a force to the latching member generally in a non-collinear direction relative to the axis of rotation to resiliently deflect another portion of the hinge pin relative to the secured portion and move the latching member in the non-collinear direction against the spring bias applied by the hinge pin and directed generally opposite to the non-collinear direction.

2. The method of claim 1 wherein the latching member is movable about the axis of rotation between an opened position in which the archwire is insertable into the archwire slot and a closed position in which the latching member retains the archwire in the archwire slot, and further comprising:

pivoting the latching member relative to the bracket body about the axis of rotation and toward the closed position.

3. The method of claim 2 wherein applying the force to the latching member further comprises:

contacting a chamfered surface on the latching member with a portion of the bracket body to generate the force applied to the latching member.

4. The method of claim 1 wherein the latching member is movable about the axis of rotation between an opened position in which the archwire is insertable into the archwire slot and a closed position in which the latching member retains the archwire in the archwire slot, and further comprising:

releasing the force to permit the spring bias to move the latching member to engage a portion of the latching member with a recess in the bracket body to secure the latching member in the closed position.

5. The method of claim 1 wherein the latching member is movable about the axis of rotation between an opened position in which the archwire is insertable into the archwire slot and a closed position in which the latching member retains the archwire in the archwire slot, and applying the force to the latching member further comprises:

when the latching member is in the closed position, using a tool to move the latching member in the non-collinear direction.

6. The method of claim 5 further comprising:

moving the latching member with the tool by an amount sufficient to release a portion of the latching member from a recess in the bracket body; and pivoting the latching member relative to the bracket body about the axis of rotation and toward the opened position.

7. The method of claim 6 further comprising:

holding the latching member in the opened position with a detent to prevent inadvertent pivoting toward the closed position.

8. The method of claim 1 wherein the latching member is movable about the axis of rotation between an opened position in which the archwire is insertable into the archwire slot and a closed position in which the latching member retains the archwire in the archwire slot, and the latching member is configured to move in the non-collinear direction when the latching member is in the closed position.

9. The method of claim 1 wherein the latching member is movable about the axis of rotation between an opened position in which the archwire is insertable into the archwire slot and a closed position in which the latching member retains the archwire in the archwire slot, and the latching member is constrained against movement in the non-collinear direction when the latching member is in the opened position.

10. The method of claim 1 wherein the orthodontic bracket does not include a structure applying a spring bias to the latching member other than the hinge pin.

* * * * *